United States Patent [19]
Gottermeier

[11] 4,336,091
[45] Jun. 22, 1982

[54] METHOD OF MAKING CAPILLARY BRIDGE IN APPARATUS FOR DETERMINING IONIC ACTIVITY

[75] Inventor: William F. Gottermeier, Pittsford, N.Y.

[73] Assignee: Eastman Kodak Company, Rochester, N.Y.

[21] Appl. No.: 189,434

[22] Filed: Sep. 22, 1980

Related U.S. Application Data

[62] Division of Ser. No. 50,845, Jun. 20, 1979, Pat. No. 4,273,639.

[51] Int. Cl.³ .................. B29D 7/02; B32B 31/18; B32B 31/30
[52] U.S. Cl. .................. 156/244.12; 156/244.18; 156/256; 156/259; 204/195 R; 204/195 F; 204/195 M

[58] Field of Search ............... 156/244.12, 244.18, 156/256, 259; 204/195 R, 195 F, 195 M

[56] References Cited

U.S. PATENT DOCUMENTS 4,184,936  1/1980  Paul et al. ............... 204/195 R Primary Examiner—Caleb Weston
Attorney, Agent, or Firm—M. S. Sales

[57] ABSTRACT

A device is disclosed for determining ion activity in liquid solutions by the use of electrodes over which a cover sheet with an internal capillary bridge promotes ionic migration between the electrodes. The cover sheet is formed of a porous material ribbon encapsulated in a nonporous web. Preferably, the cover sheet is punched at each electrode to provide fluid access holes for receiving drops of liquid solutions.

6 Claims, 10 Drawing Figures

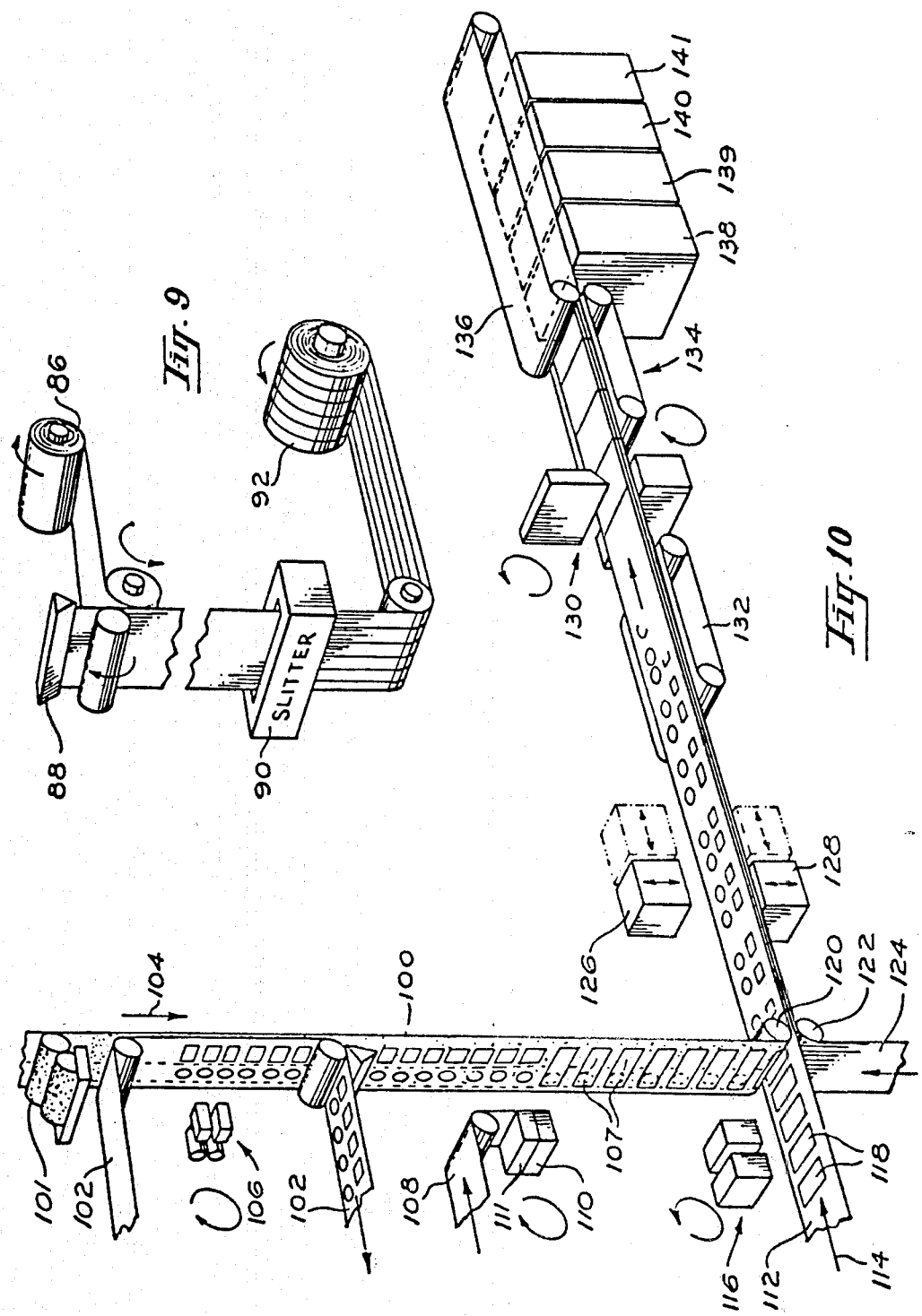

METHOD OF MAKING CAPILLARY BRIDGE IN APPARATUS FOR DETERMINING IONIC ACTIVITY

This is a division of application Ser. No. 50,845, filed June 20, 1979, now U.S. Pat. No. 4,273,639.

BACKGROUND OF THE INVENTION

1. Cross Reference to Related Applications

Reference is made to commonly assigned, U.S. Pat. No. 4,184,936 entitled DEVICE FOR DETERMINING IONIC ACTIVITY, filed in the names of J. O. Paul and K. Babaoglu on July 24, 1978.

2. Field of the Invention

The present invention relates to devices useful in determining the activity of an ionic analyte of an aqueous solution, and is particularly useful in potentiometrically measuring ion activity in drops of biological fluids.

3. Description of the Prior Art

There is a variety of apparatus in the prior art for measuring ion activity in solutions. A test device incorporating ion-selective electrodes which develop an electrical potential proportional to the logarithm of the activity of the ions to which the electrodes are sensitive is described in the abovementioned commonly assigned U.S. Pat. No. 4,184,936 and is shown at 10 in FIG. 1 of the accompanying drawings. Two solid electrodes 12 and 14 are mounted on a frame 16, and a capillary bridge 18 is provided for promoting ionic migration between two fluid access holes 20 and 22 at the electrodes. The capillary bridge includes a nonporous support layer, a porous layer with ionic access to both electrodes, and a top nonporous cover layer which is preferably hydrophobic. When a drop of reference solution of known ion activity is applied to one fluid access hole and a drop of test solution is applied to the other fluid access hole, the drops spread into the porous layer until contact is made at a thin junction interface, permitting ionic migration between the drops. An electrometer 24 is provided to measure the electrical potentials at the interfaces between each solution drop and its associated electrode to provide an indication of ion activity in the test solution.

Although the device disclosed in U.S. Pat. No. 4,184,936 provides excellent results in determining ion activity in liquids, the present invention is an improvement which provides advantages in both assembly and performance. As can be seen in FIG. 1, capillary bridge 18 is a small discrete part which must be both accurately placed on the electrodes during assembly and held in place by an adhesive. These constraints increase assembly problems and potentially decrease performance due to possible misalignment of the fluid access holes and failure of the adhesive bond. Further, fluid leakage from the edge of the bridge could effect the area of wetted electrode surface because the edges of the bridge are aligned with the electrodes. Unpredictability of the total area of wetted electrode surface would adversely affect the test results.

SUMMARY OF THE INVENTION

In accordance with the present invention, a device is provided for determining the activity of an ionic analyte of an aqueous solution wherein two electrodes are held in a frame by an integral cover sheet and capillary bridge. The cover sheet is formed of a nonporous material with an encapsulated porous ribbon, and fluid access holes extend through the cover sheet in alignment with the porous ribbon and each electrode. The test and reference fluids are confined to the porous ribbon to form an ion junction between the electrodes.

In accordance with one embodiment of the present invention, the cover sheet is formed by encapsulating a ribbon of porous material in the cross section of a plastic web by a two-pass extrusion process. The porous material is located only in an area along a line generally corresponding to the common centerline of both fluid access holes. Vents are provided in the cover sheet to allow air in the bridge to be displaced by the advancing liquid wave fronts when test and reference solutions are applied at the fluid access holes.

According to another embodiment of the present invention, the cover sheet is formed by coating one side of a porous ribbon with a plastic material and then pressing the coated ribbon into a film of nonporous material.

The present invention permits assembly machines to be significantly less complex because the assembled ion-selective electrode test device has fewer components and the need to accurately locate a small discrete capillary bridge has been eliminated. As a result, test devices manufactured in accordance with the present invention exhibit exceptionally large drop placement latitude (i.e., a drop of liquid may be placed upon the device anywhere over a large area and still wet the electrode area) because the simplified assembly process allows the fluid access hole locations to be more accurately controlled. This feature is important in permitting relaxed manufacturing tolerances in automatic processing apparatus wherein the drops are applied mechanically.

Further, fluid leakage from the edge of the bridge will not affect the area of wetted electrode surface because the edges of the bridge of the present invention are not aligned with the electrodes.

The invention, and its objects and advantages, will become more apparent in the detailed description of the preferred embodiments presented below.

BRIEF DESCRIPTION OF THE DRAWINGS

In the detailed description of the preferred embodiments of the invention presented below, reference is made to the accompanying drawings in which:

FIGS. 8 and 9 are schematic illustrations of how another embodiment of the cover sheet is fabricated; and FIG. 10 schematically shows the assembly of devices according to the present invention.

DESCRIPTION OF THE PREFERRED EMBODIMENTS

Although the invention as hereinafter described is directed to a device for potentiometrically determining ion activity through the use of ion-selective electrodes, such device can be used for other electrical tests of a liquid solution. The device is particularly adapted for processing by automated handling equipment.

Figure 2:
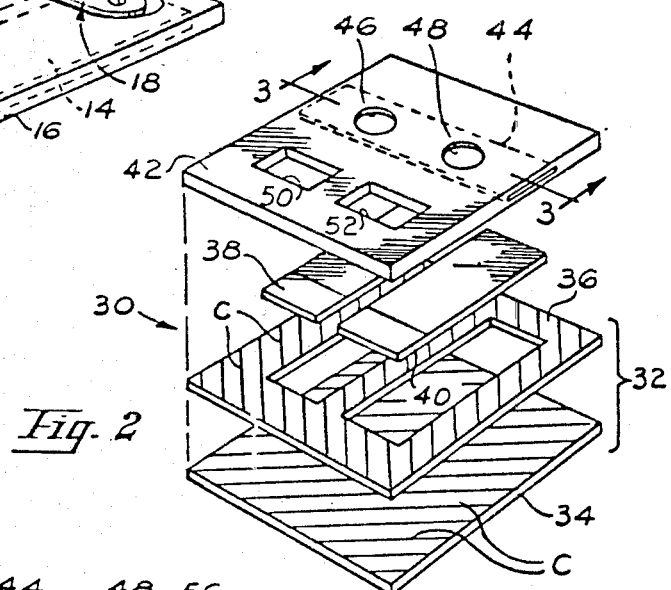
FIG. 2 is an exploded perspective view of a device for determining the activity of an ionic analyte of an aqueous solution constructed in accordance with the present invention.

FIG. 2 illustrates in exploded perspective a device 30 which has an electrically insulative mounting frame 32 formed of a base web 34 and a spacer web 36. Two solid electrodes 38 and 40 are mounted in the frame and electrically isolated from each other. A cover sheet 42, with an internal capillary bridge 44, promotes ionic migration between solution drops deposited in fluid access holes 46 and 48. The fluid access holes extend through the cover sheet in the region of electrodes 38 and 40. Two electrical access holes 50 and 52 are also formed in the cover sheet.

THE ELECTRODES

Figure 1:
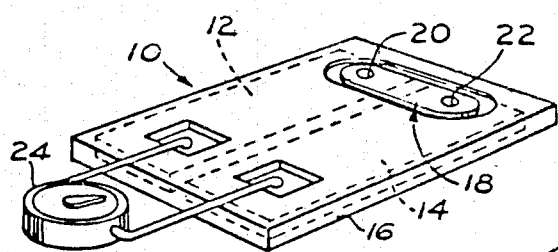
FIG. 1 is a perspective view of a device for determining the activity of an ionic analyte of an aqueous solution constructed in accordance with the prior art.
Figure 3:
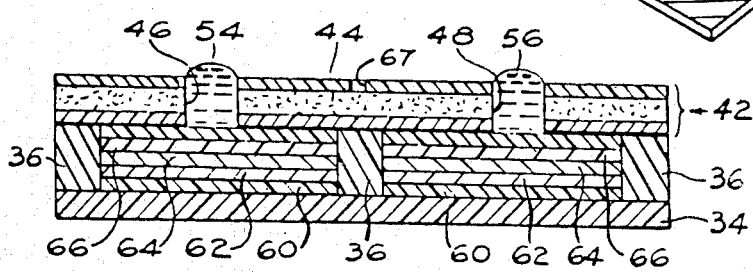
FIG. 3 is an assembled sectional view taken generally along the line designated as 3—3 in FIG. 2.

Electrodes 38 and 40 are either respectively an ion-selective electrode and an external reference electrode, for a direct mode of determining potentials, or respectively two ion-selective electrodes for a differential measurement comparing the ion activity of an unknown test solution with that of a similar reference solution of known ion concentration. Electrodes 38 and 40 are shown as being identical and, therefore, suitable for the differential mode of measurement which is made by electrometer 24 (FIG. 1) when a test drop 54 (FIG. 3) is applied to one electrode and a reference drop 56 having a known concentration of ions is applied to the other electrode. In FIG. 3, the thickness of the layers of the electrodes has been greatly exaggerated for clarity.

Both electrodes are formed of layers comprising an ion-selective membrane 58 (permeable to the ion of choice) coated over a multilayer internal reference element which in turn is coated over a support 60, all of which are solid layers. Each internal reference element is shown as comprising several layers such as metal layer 62, layer 64 which is an insoluble salt of the metal of layer 62, and layer 66 which is an electrolyte containing layer. Although the layers are generally referred to as being "coated" one over another, it should be understood that the term "coating" is meant to include laminating or otherwise forming the various strata one over another by any technique.

For purposes of describing the present invention, it is believed that a detailed discussion of the structure and operation of electrodes 38 and 40 is not necessary. However, a full description of various embodiments of such electrodes and the method of use thereof may be found in co-assigned U.S. Pat. No. 4,053,381. The disclosure of that patent is specifically incorporated herein by reference.

THE COVER SHEET AND CAPILLARY BRIDGE

Cover sheet 42 is shown in FIG. 2 and in section in FIG. 3. The cover sheet is preferably a flat, composite web having through-holes 46, 48, 50, and 52. A ribbon of porous material is encapsulated in the cover sheet to form capillary bridge 44 between fluid access holes 46 and 48 as a means of promoting ionic migration between electrodes 38 and 40. Bridge 44 in a preferred embodiment is a porous paper into which liquid drops 54 and 56 are absorbed to form an ionic junction. A suitable paper for correct absorption of human serum is Whatman #2 chroma, 0.007 inch thick, which is manufactured in the United Kingdom by W. and R. Balston, Ltd. When spotted with liquid solution drops at holes 46 and 48, the liquid fills the holes, forms large caps on cover sheet 42, and within 10 to 30 seconds is absorbed into the paper.

Another example of a material suitable for the porous ribbon is disclosed in referenced U.S. Pat. No. 4,053,381. However, other porous material which is resistant to becoming clogged by the plastic overcoats will readily occur to those skilled in the art. Throughout this specification and the appended claims, the porous material which forms capillary bridge 44 is referred to as a ribbon, and that is meant to define any elongated form such as, for example, a web, a thread, threads, a strip, etc.

The liquid from each drop spreads into capillary bridge 44 until contact is made at about the middle of the bridge to form an ionic junction. Preferably, sufficient liquid is left unabsorbed to fill holes 46 and 48. It is desirable to vent the cover sheet to assure rapid junction formation. Vents, such as shown at 67 in FIG. 3, allow air trapped in the porous material to escape and be displaced by the advancing liquid wave fronts from the fluid access holes. Venting can be accomplished by puncturing the top plastic covering to expose the porous material to the atmosphere. Optimally, vents should be spaced along the entire bridge area between the fluid access holes. This design is better than having vent holes only in the center of the bridge because in this latter case, the vent holes could be sealed off before liquid junction formation. This condition would be augmented when the flow rates from the test and reference drops were significantly different.

Capillary bridge 44 is preferably located only in an area along a line which corresponds to the common center-line of fluid access holes 46 and 48. Generally, the porous material which forms the capillary bridge cannot be used as a full cover sheet because the additional volume would result in too large a fluid capacity.

OPERATION

Operation of the device is described in U.S. Pat. No. 4,053,381, and in general proceeds by spotting a drop of the reference solution in hole 46 and a drop of the test solution in hole 48. Probes contact electrodes 38 and 40 (FIG. 1), and the potentials are read on electrometer 24. The reading indicates ion activity in the test solution.

The test device is then removed from contact with electrometer 24 and disposed of, and a new device is positioned to receive subsequent drops of solution and to contact the electrometer leads.

COVER SHEET FABRICATION—FIRST EMBODIMENT

Reference is made to FIGS. 4–7 for a schematic illustration of the fabrication of an elongated web from which a plurality of cover sheets 42 are produced. A roll 70 of suitable porous material for capillary bridge 44 is positioned adjacent to an extrusion die 72, and the porous material is drawn under the die into contact with a film 74 of molten plastic. Film 74 may be polystyrene, but any plastic which can be formed into a free film would be acceptable.

Before film 74 is completely quenched, the composite web of porous material from roll 70 and plastic film 74 is calendered between a pair of rollers 76 and 78. The resultant composite web 80 has a uniform thickness (as shown in cross section in FIG. 5) and is wound into a roll 82.

Figures 4, 6:
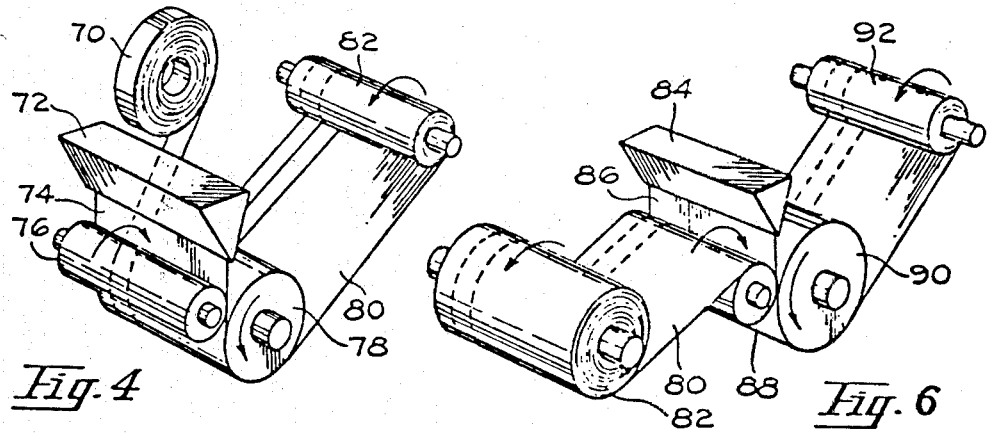
FIGS. 4–7 are schematic illustrations of how one embodiment of the cover sheet is fabricated.
Figure 5:
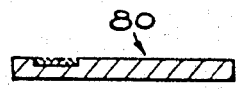
Figure 7:
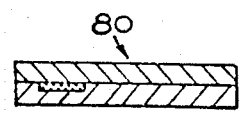

Referring to FIG. 6, composite web 80 is next unwound from roll 82 and drawn under an extrusion die 84 into contact with another free film 86 of molten plastic so that the side of web 80 into which the porous material has been pressed is overcoated with a layer of plastic as the web passes between rollers 88 and 90 and is wound into a roll 92. A cross sectional view of the final web is shown in FIG. 7.

Several variations of the above process are within the scope of the present invention. For example, multiple parallel ribbons of porous material can be encapsulated into a wide plastic web. The wide web would then be split between the strands. Further, the need for a two-pass operation could be eliminated by use of multiple coating dies or a crosshead die.

COVER SHEET FABRICATION—SECOND EMBODIMENT

Figure 8:
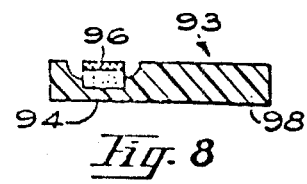

FIG. 8 is a cross-sectional view of a composite web formed in accordance with another embodiment of the present invention. As shown in FIG. 9, a web of porous material from a supply roll 86 is coated with polyethylene from an extrusion die 88. After the polyethylene has been quenched, the web is slit into ribbons at 90 and wound into a plurality of rolls 92.

When the coated web of porous material is drawn under an extrusion die similar to die 72 of FIG. 4 and calendered with the polyethylene coating facing away from free film 74 of molten polystyrene, a composite web 93 as shown in FIG. 8 is formed. In that figure, the porous material is denoted by reference numeral 94, its polyethylene coating by numeral 96, and the quenched polystyrene base by numeral 98.

The cover sheet formed by this process has inherent ventilation because the polystyrene of base 98 does not bond to the polyethylene of coating 96 during the extrusion process. The exposed porous material at the edge of coating 96 provides a venting path to allow air to escape from the bridge as it is displaced by liquid absorbed by the bridge. If additional venting is desired, it can be more easily implemented than in the case of the FIGS. 4–7 embodiment because coating 96 in thinner than the second extrusion layer of the previous embodiment.

ASSEMBLY OF THE DEVICE

The integral capillary bridge and cover sheet eliminates or simplifies a number of slide assembly steps inherent in devices having discrete bridges. Thus, assembly machines can be significantly less complex.

FIG. 10 schematically shows how the devices can be assembled when an integral bridge and cover sheet is used. All of the materials except the ion-selective electrodes are assembled by simply laminating continuous webs of material together and chopping finished slides from the resulting web.

A web 100, which has been manufactured and slit in accordance with, for example, any of the previously described embodiments, is coated at 101 on one side with an adhesive and covered by an interleaving material 102. This composite web is moved continuously in the direction of arrow 104 past a set of punches 106 which moves cyclically to perforate the web, forming round fluid access holes 46 and 48 and rectangular electrical access holes 50 and 52 (FIG. 2).

Following punching station 106, interleaving material 102 is stripped from web 100 to expose the adhesive coating. Ion-selective electrodes 107, which are chopped from a web 108 by punches 110 and 111, are applied to the adhesive in alignment with the fluid and electrical access holes. Punches 110 and 111 are close together when they punch web 108 to eliminate waste.

As the punches move toward web 100 to deposit the electrodes, the punches separate so that the electrodes are spaced apart. The adhesive coating on web 100 holds the ion-selective electrodes in position and creates a seal around the fluid access holes to prevent the reference and sample fluids from spreading between the cover sheet and the ion-selective electrodes of FIG. 2.

A spacer web 112 is moved in the direction of arrow 114 from a stock roll, not shown. The spacer web has a plurality of ultrasonic energy concentrators on its upper surface. The concentrators are schematically shown as lines c on web 36 in FIG. 2 and aid in the welding process specified hereinafter. As web 112 passes under a pair of punches 116, rectangular holes 118 are punched to align with ion-selective electrodes 107 on web 100 when the two webs join between a pair of rollers 120 and 122.

A third web 124 also passes between rollers 120 and 122 to join with the other two webs. The third web also has ultrasonic energy concentrators c as shown schematically in FIG. 2 and forms base web 34 (FIG. 2) in the finished device.

An ultrasonic horn or horns 126 and anvil or anvils 128 are movable into engagement with, and then along with, the composite web to weld the webs together. The presence of the high energy concentrators between individual webs 100, 112, and 124 increase the welding operation's efficiency.

The joined webs are translated from the welding station to a knife press 130 by a continuously moving vacuum belt drive 132. Knife press 130 has a rotary motion to chop the joined webs into individual slides which are moved by a slide spacer belt 134 to a slide selecting vacuum belt 136. Belt 136 carries the slide above bins 138–141 for sorting as desired. For example, bin 138 could receive slide rejects, bin 139 might receive randomly selected slides for quality control testing, and bins 140 and 141 would be filled with slides for commercial sale.

ADVANTAGE OF THE FULL COVER SHEET WITH BRIDGE

The intergral cover sheet and porous bridge in accordance with the present invention reduces the number of slide components and offers a major slide assembly advantage by eliminating the need for the slower and waste prone process of placing discrete bridge units onto the partially assembled slide. Further, the integral cover sheet minimizes performance problems such as fluid leakage onto the ion-selective electrodes and increased drop placement latitude.

Fluid leakage from the edge of the porous bridge of the intergral cover sheet will not increase the area of wetted electrode surface because the edge of the bridge is isolated from the ion-selective electrodes. Accordingly, test results will not be affected by such leakage.

Further, an integral cover sheet permits more accurate fluid access hole placement than in the case where an ionic bridge must be placed on the slide as a discrete part. Accurate fluid access hole placement increases drop placement latitude.

Another advantage of the present invention is derived from the fact that the cover sheet is mechanically held to the slide by an ultrasonic seal around its entire perimeter. Spacer web 36 is slightly thinner than electrodes 38 and 40 so that the cover sheet and electrodes are pressed together. Thus, the adhesive coating on the cover sheet serves primarily as a fluid seal and does not have to be strong enough to hold the bridge and electrodes together, thereby decreasing the risk of delamination of the bridge and fluid leakage thereunder.

The invention has been described in detail with particular reference to preferred embodiments thereof, but it will be understood that variations and modifications can be effected within the spirit and scope of the invention.

What is claimed is:

1. A method for making a device which includes (1) a pair of solid electrodes for generating therein an electrical potential having a predetermined relationship to the amount of ionic analyte activity present in a contacting sample of an aqueous solution, and (2) a frame member; said member comprising the steps of:

encapsulating an elongated ribbon of porous material in nonporous material which is sized to substantially cover the frame member;
   applying the electrodes in a spaced-apart relationship to the frame member;
   forming a pair of holes in said nonporous material through the ribbon of porous material; and
   bonding said nonporous material to the frame member with the electrodes therebetween in an orientation such that each of said holes aligns with a different electrode.

2. A method for making a device which includes a pair of solid electrodes constructed to develop therein an electrical potential having a predetermined relationship to the amount of ionic analyte activity present in a contacting sample of an aqueous solution; said method comprising:

encapsulating an elongated ribbon of porous material lengthwise within an elongated web of nonporous material;
   forming a series of holes in said nonporous material through said ribbon of porous material;
   applying the electrodes to said web of nonporous material in an orientation such that each of said holes aligns with a different electrode;
   joining to said web a frame member of electrically nonconductive material with the electrodes sandwiched therebetween to form a composite strip; and
   severing said composite strip into individual devices having two of said holes and two of said electrodes each.

3. A method for making a device which includes a pair of solid electrodes constructed to develop therein an electrical potential having a predetermined relationship to the amount of ionic analyte activity present in a contacting sample of an aqueous solution; said method comprising:

encapsulating an elongated ribbon of porous material lengthwise within an elongated web of nonporous material by the steps of (1) extruding nonporous material to form a film of such material, (2) calendering said film and said elongated ribbon of porous material between a pair of rollers to form a composite web of nonporous material with said ribbon of porous material embedded in one surface thereof, and (3) drawing said composite web under an extrusion die with said one surface in contact with another film of nonporous material from said extrusion die, whereby said one surface is overcoated with a layer of nonporous material;
   forming a series of holes in said nonporous material through said ribbon of porous material;
   applying the electrodes to said web of nonporous material in an orientation such that each of said holes aligns with a different electrode;
   joining to said web a frame member of electrically nonconductive material with the electrodes sandwiched therebetween to form a composite strip; and
   severing said composite strip into individual devices having two of said holes and two of said electrodes each.

4. A method for making a device which includes a pair of solid electrodes constructed to develop therein an electrical potential having a predetermined relationship to the amount of ionic analyte activity present in a contacting sample of an aqueous solution; said method comprising:

encapsulating an elongated ribbon of porous material lengthwise within an elongated web of nonporous material by the steps of (1) drawing the ribbon of porous material under an extrusion die in contact with a first film of nonporous material discharged from said extrusion die, whereby said ribbon of porous material is coated on one side by said first film, (2) extruding a second film of nonporous material wider than said ribbon of porous material and coating, and (3) calendering the coated ribbon of porous material and said second film between a pair of rollers with the first coating facing away from said second film to form a composite web of nonporous material with said ribbon of porous material encapsulated between said nonporous webs;
   forming a series of holes in said nonporous material through said ribbon of porous material;
   applying the electrodes to said web of nonporous material in an orientation such that each of said holes aligns with a different electrode;
   joining to said web a frame member of electrically nonconductive material with the electrodes sandwiched therebetween to form a composite strip; and
   severing said composite strip into individual devices having two of said holes and two of said electrodes each.

5. The method as defined in claim 4 wherein said first and second films are formed of different, nonbonding material.

6. The method as defined in claim 4 wherein:
   said first film is formed of polyethylene; and
   said second film is formed of polystyrene.

* * * * *

UNITED STATES PATENT AND TRADEMARK OFFICE
CERTIFICATE OF CORRECTION

PATENT NO. : 4,336,091
DATED : June 22, 1982
INVENTOR(S) : W. F. Gottermeier

It is certified that error appears in the above—identified patent and that said Letters Patent is hereby corrected as shown below:

Column 5, line 38, delete "in" and insert --is--.

Column 7, line 15, delete "member" and insert --method--.

Signed and Sealed this

Second Day of November 1982

[SEAL]

Attest:

GERALD J. MOSSINGHOFF

Attesting Officer    Commissioner of Patents and Trademarks